US006783084B1

(12) United States Patent
Nelson

(10) Patent No.: US 6,783,084 B1
(45) Date of Patent: Aug. 31, 2004

(54) METHOD AND APPARATUS FOR OLFACTORY STIMULATION

(76) Inventor: R. Douglas Nelson, 151 N. Alvardo Ave., Ojai, CA (US) 93023

( * ) Notice: Subject to any disclaimer, the term of this patent is extended or adjusted under 35 U.S.C. 154(b) by 100 days.

(21) Appl. No.: 09/988,823

(22) Filed: Nov. 20, 2001

Related U.S. Application Data

(60) Provisional application No. 60/249,467, filed on Nov. 20, 2000.

(51) Int. Cl.[7] ............................................... A62C 13/62
(52) U.S. Cl. ...................... 239/307; 239/304; 239/305; 239/340; 239/346; 239/369; 352/85
(58) Field of Search ................................. 239/303, 304, 239/305, 307, 326, 346, 340, 369, 419, 433; 352/85; 261/76, 78.1, DIG. 65; 128/203.12

(56) References Cited

U.S. PATENT DOCUMENTS

| 2,905,049 | A | * | 9/1959 | Laube ........................ 352/85 |
| 3,628,829 | A |  | 12/1971 | Heilig |
| 4,603,030 | A | * | 7/1986 | McCarthy ............ 261/DIG. 65 |
| 5,109,839 | A | * | 5/1992 | Blasdell et al. ......... 128/203.12 |
| 5,610,674 | A | * | 3/1997 | Martin ........................ 352/85 |
| 5,769,725 | A |  | 6/1998 | Ogden et al. |
| 5,807,114 | A |  | 9/1998 | Hodges et al. |
| 6,169,595 | B1 | * | 1/2001 | Manne ........................ 352/85 |
| 6,584,374 | B2 | * | 6/2003 | Lee et al. ..................... 352/85 |

* cited by examiner

Primary Examiner—Steven J. Ganey
(74) Attorney, Agent, or Firm—Dowell & Dowell, P.C.

(57) ABSTRACT

A method and apparatus for delivering aromatic substances for olfactory stimulation, treatment and/or therapy which includes a delivery assembly including a chamber into which air is introduced and subsequently delivered under even pressure through a mixing venturi. A plurality of conveying conduits are selectively communicated with the venturi so that aromatic substances are entrained in the air passing through the venturi to a discharge mask or zone. The conduits communicate with a plurality of containers of aromatic liquids, solids, and semi-solids. The containers are subject to selective introduction of pressurized air by way of a plurality of valves. A system is provided for controlling the operation of the valves to thereby control the substances discharged from the apparatus.

20 Claims, 7 Drawing Sheets

METHOD AND APPARATUS FOR OLFACTORY STIMULATION

This application claims the benefit of U.S. Provisional Patent Application, Serial No. 60/249,467 which was filed on Nov. 20, 2000 by the same title and same inventor.

BACKGROUND OF THE INVENTION

Field of the Invention

This invention is generally directed to olfactory stimulation and therapeutic devices and more particularly to a method and apparatus for delivering various aromas and essences, or a combination of essences and aromatics to an individual for purposes of olfactory stimulation and or therapy wherein the supply of aromatics can be regulated and controlled to provide for an optimization of treatment, therapy, mood alteration, and for use with various forms of entertainment, including virtual reality, games and simulations.

BRIEF DESCRIPTION OF THE DRAWINGS

A better understanding of the invention will be had with respect to the attached drawings wherein.

DESCRIPTION OF THE PREFERRED EMBODIMENT

Figure 1:
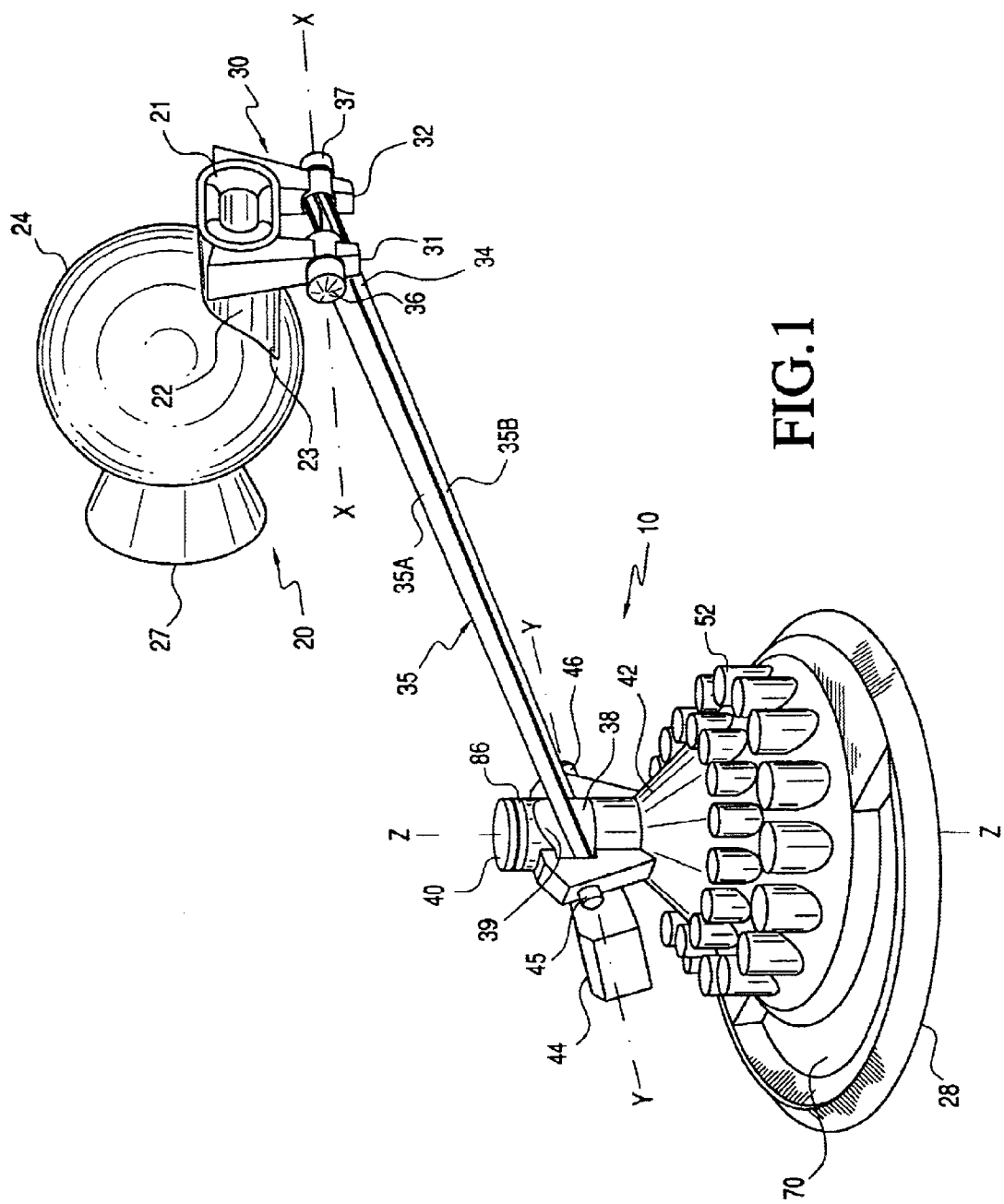
FIG. 1 is a front perspective view of the olfactory stimulation and therapeutic device of the present invention.

In accordance with the method of the present invention, one or a mixture of substances including aromas, essences, essential oils and scents are selectively supplied from a plurality of containers to a delivery system. The delivery includes a plurality of tubes or conduits which extend from the containers to a mixing venturi disposed relative to a discharge of the system by way of which single substances and/or mixtures thereof are directed to an individual for purposes of aromatic treatment, therapy, mood alteration, and for use with various forms of entertainment including virtual reality, games and simulations. The flow path of the aromatics from the containers to the venturi is specifically designed to ensure that all fluid flow is maintained such that there is an upward vertical component of movement so that when flow is terminated through any of the conduits, any condensates will flow by gravity back to the containers. In addition, in the preferred embodiments, the aromatics under pressure are selectively discharged into the venturi by way of pressure responsive injection valves which are oriented at least partially in an upward vertically direction such that any condensates from the valves also flow by gravity therefrom through the conduits and the containers, when the injection valves are closed, thus ensuring the area of the venturi does not become contaminated with an aromatic once dispensing of such an aromatic has ceased. Because of the gravity drain of condensed aromatics, whenever the control system of the invention deactivates or terminates the supply of a given aromatic into the venturi for discharge, that given aromatic will not adversely affect the aromatic or combination of aromatics being subsequently supplied to an individual from the delivery system. Thus, with the invention, instantaneous changes in olfactory stimulation and/or treatment are ensured.

In keeping with the method of the invention, containers of aromatics are communicated by way of supply valves to a source of air pressure. By appropriate and selective activation of the supply valves, air under adjustable pressures is communicated with one or more of the containers to entrain the essences, oils or other aromatics which may include liquids, gels, solids and semi-solids into a gaseous flow through the delivery conduits and to the injection valves of the mixing venturi. Another source of air flow is established, in a preferred embodiment, into a plenum chamber upstream of the venturi. Air flow into the plenum chamber is preferably passed through a filter before entering the plenum. Thereafter, the purified air is conveyed to the venturi at which time selected aromatics are entrained within the air flow to the discharge of the apparatus by predetermined operation of the injection valves.

Although the deliver system may be constructed and designed as a stationary unit wherein a patient or an individual receiving aromatherapy may be positioned relative to the discharge of the system, in preferred embodiments, the discharge assembly of the system is adjustably mounted to allow accurate positioning of the aromatic air discharged so as to ensure the discharge is properly directed for each individual. In this respect, it is in keeping with the methodology of the invention that a discharge head assembly be pivotally mounted about at least one and preferably two pivot axes. In one preferred embodiment, the discharge head assembly is mounted about a first pivot axis to a boom through which the aroma conduits extend. The boom may be additional pivotally mounted relative to a base by way of a housing which itself is rotatably mounted to swivel or rotate relative to the base. Through such a mounting system, the discharge head assembly may be somewhat universally adjustable. However, such adjustments are constrained mechanically to ensure that the vertical component and orientation of the aroma conveying conduits and the deliver injection valves are maintained to provide for the gravity drain, as previously described.

As described, the deliver system is controlled by a controller which may be manually operated and/or computer operated. Using a manual controller, an aromatherapist or other professional may selectively operate varying combinations and sequences of supply valve operations through an appropriate control panel which may be directed mounted to the base of the system or connected thereto by electrical connector or cord including telephone or other communication lines, a radio frequency transmitter/receiver or light source transmitter and sensor.

Using a computer controller alone or in combination with a manual controller also permits programming and compiling of information to thereby create predetermined control and sequency of the supply valves to affect the olfactory responses of a patient or individual receiving treatment. By treating a patient's response to various sensed conditions of aromatic blends, a library can be created for each individual or patient which can be used to maximize the desired beneficial and/or therapeutic response desired for the aromatic treatment. Patient response can be determined by a variety of sensors which may be attached to the patient. Information from such sensors can be inputted into a computer processor to develop software to allow a therapist to individualize each patient's treatment. Also, the systems of the invention may be used concurrently with other sensory display devices to further adapt the treatment to maximize patient response. Such other sensory display devices may include audio, visual, motion, touch or other devices for stimulating and changing a patient's response to a variety of sensory inputs which can occur in combination with the olfactory treatment, thereby providing a further benefit for patient treatment.

With continued reference to the drawings, the olfactory therapy and stimulation system of the invention includes a delivery apparatus or machine 10 which, in the embodiment shown, includes an aromatic delivery head assembly 20 including a discharge mask outlet 21 through which a mixture of air and various aromatics are discharged to an individual or patient. The discharge mask 21 is provided at a downstream end of a mixing chamber or venturi nozzle 22 which is connected at its opposite end, or intake end, 23 to a plenum chamber 24. In the drawing figures the plenum chamber is shown as being generally spherical, however, other shapes can be used, it being the object of the plenum to receive air inputted from a blower or fan 25, after the air is drawn through a filter 26 at an intake 27. Within the plenum, the pressure of the air is equalized such that a constant pressure of air is caused to flow to the inlet end 23 of the mixing venturi so that the flow through the venturi is maintained relatively constant depending upon the speed selected for the fan or blower. The rate of air flow may be selectively controlled using a blower controller mounted within base 28 of the machine.

The head assembly is carried by a bracket 30 having opposite arms 31 and 32 which are mounted to the venturi nozzle 22 and which are pivotally connected to an outer and upper end 34 of a boom 35. Knobs 36 and 37 are provided to allow the adjustment and subsequent securing of the bracket and thus the head assembly in a predetermined position about an axis of rotation X—X. The boom 35 is hollow including upper and lower removable covers 35A and 35B for purposes of housing aroma, fragrance, or scent conveying conduits 62 which extend between the arms to the venturi, as will be described.

The boom is pivotally mounted about an axis Y—Y to a pivot shaft 38 adjacent its lower end through an opening 39 in a crown assembly 40 mounted on, or extending upwardly from, a housing 42. The housing is rotatably mounted about a vertical axis Z—Z to the base 28 of the machine. A counterweight 44 is provided at the lower end of the boom 35 to stabilize the dispensing or delivery head 20. Knobs 45 and 46 are associated with pivot shaft 38 in order to secure the boom in a predetermined angular orientation with respect to the vertical axis Z—Z. The opening 39 in the crown 40 is provided with an inclined or beveled surface which is angled upwardly toward the delivery head 20 such that the boom can not be lowered below about 10° above a horizontal plane to thereby ensure the vertical component of orientation of the boom and head assembly for purposes of facilitating drainage of the aromatic conduits, as previously described.

Figure 2:
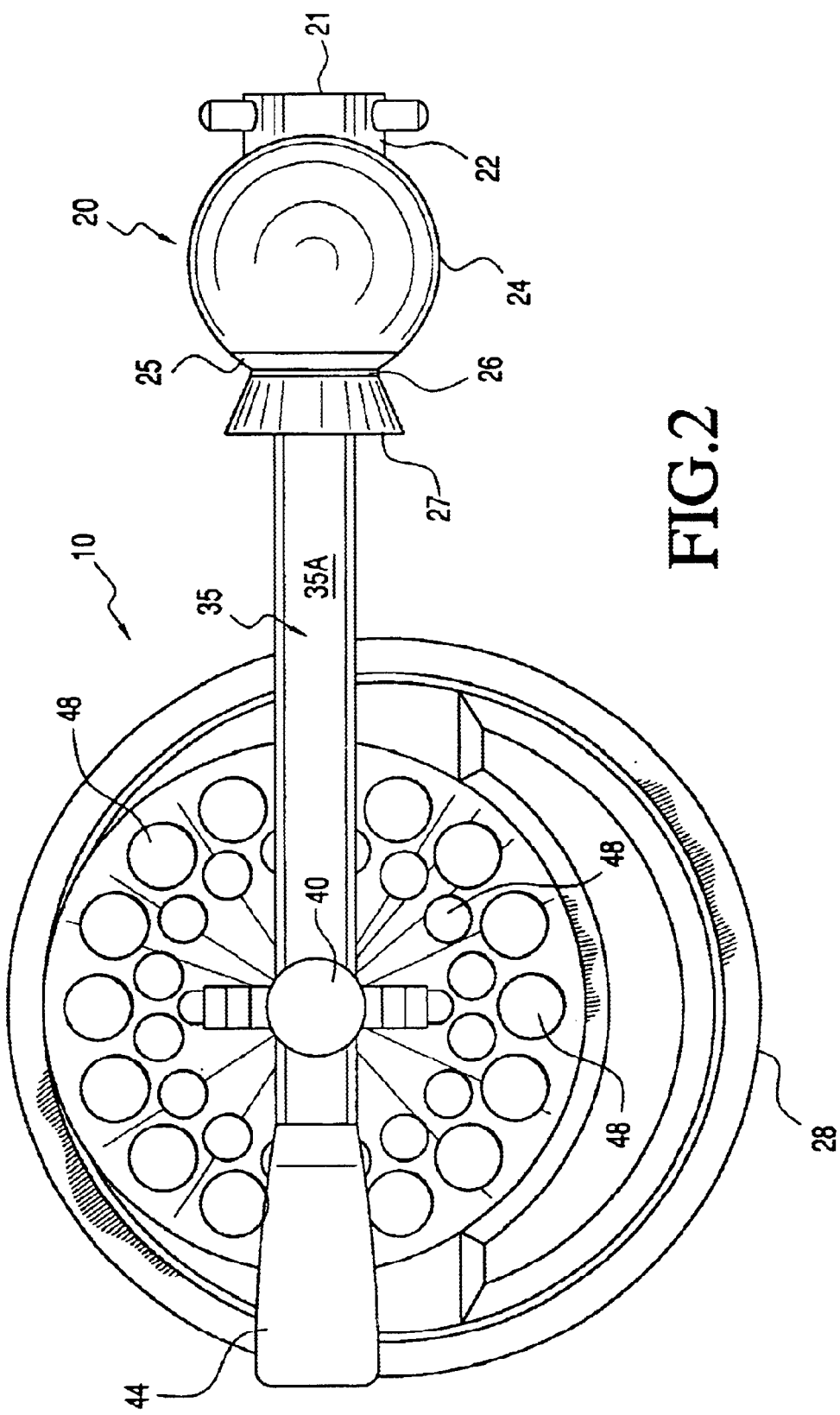
FIG. 2 is a top plan view thereof showing containers removed from pockets in a hollow housing of the base of the device.
Figure 3A:
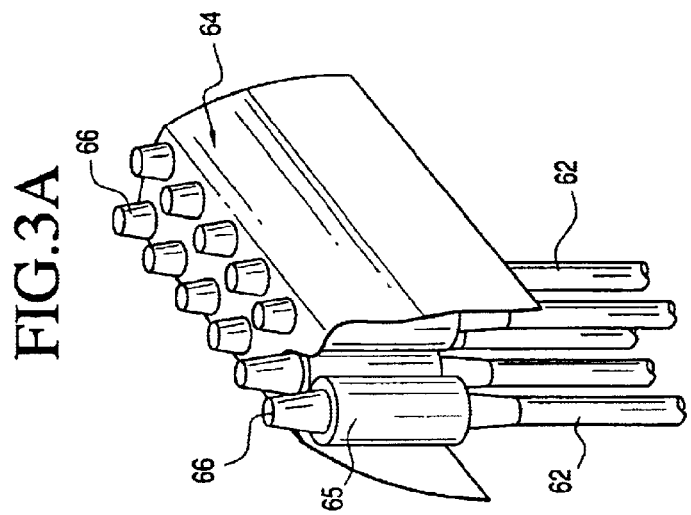
FIG. 3A is a partial perspective view of the injectors and conduits shown in FIG. 3.
Figure 3:
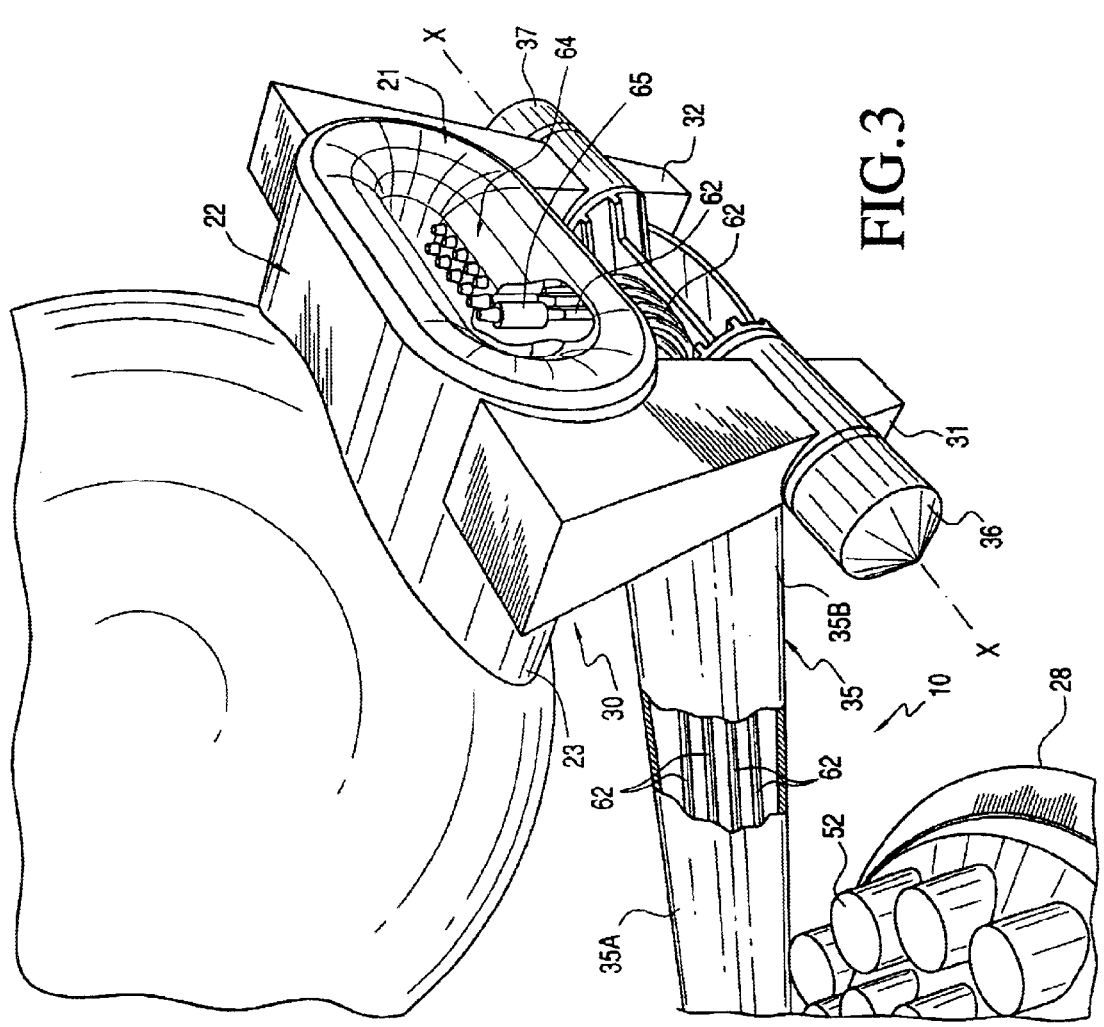
FIG. 3 is an enlarged partial perspective view showing aromatic conduits and pressure injectors associated with the olfactory stimulation and therapeutic device of the present invention.
Figure 4:
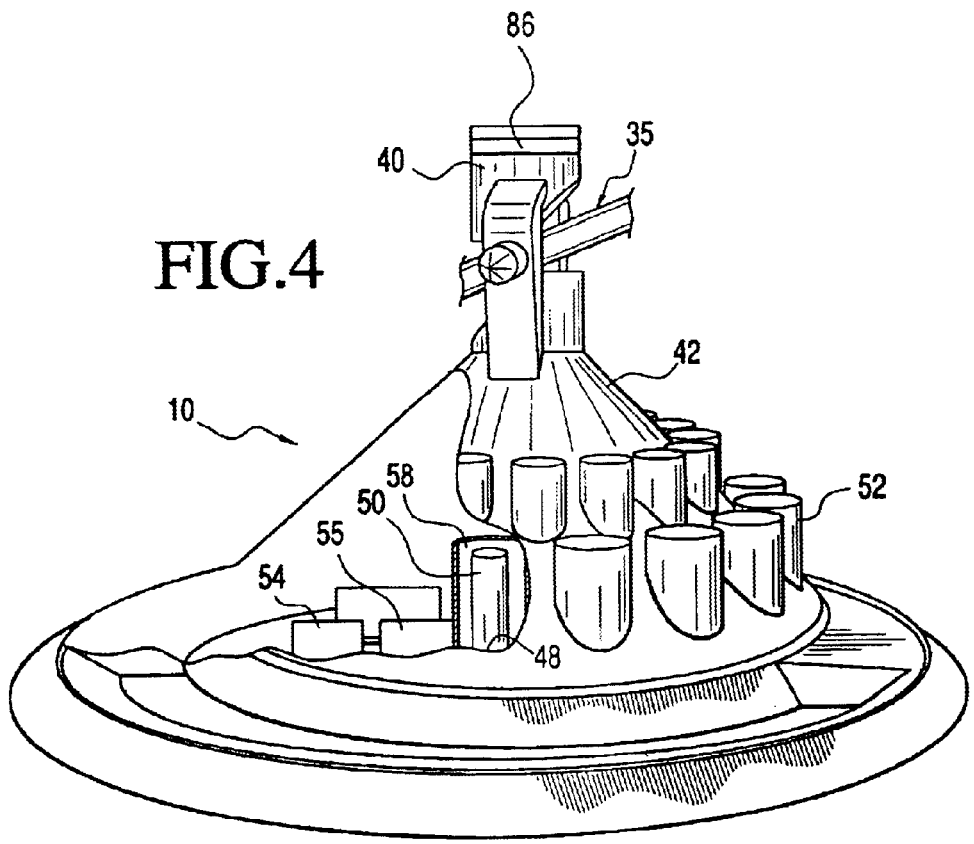
FIG. 4 is a front plan view of the device of FIG. 1 having portions broken away to show one of the aroma containers mounted with respect to the housing of the device.

The housing 42 has a plurality of open pockets 48 formed therein for receiving containers 50, see FIGS. 2 and 4, of various aromatics, fragrances, and essences. The containers are covered by transparent covers 52 so that visual inspection can easily determine when a container should be refilled or replaced. The covers are friction fitted so as to seat within the pockets 48 to thereby prevent release of aromatics therefrom.

Figure 5:
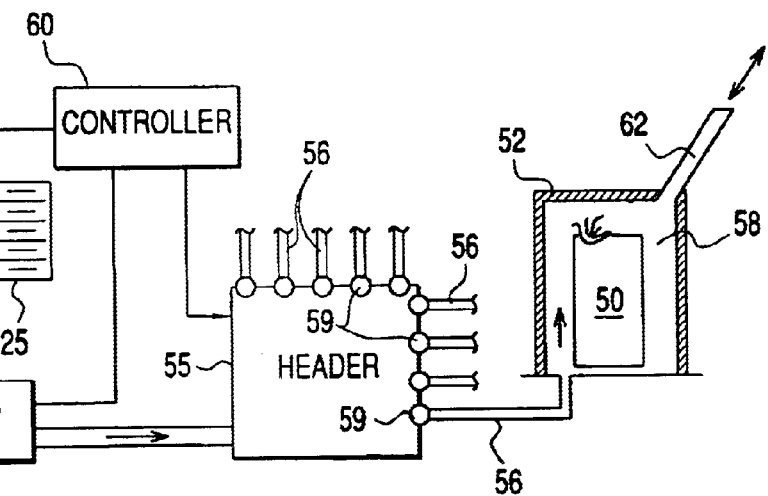
FIG. 5 is a diagram showing the relationship between the controller, motors, air pump and air injection headers associated with the present invention.

With particular reference to FIG. 5, an air supply pump or other pressurized air supply source 54 is mounted within the housing 42 and is connected to a suitable source electrical supply (not shown) and to a controller 60, as will be described. The pump 54 is connected through an air supply header 55 to a plurality of tubes 56 which extend from the header to chambers 58 created between each of the containers So and their covers 52. A plurality of electro-mechanical valves 59 are provided in the header 55 and are operated by the controller 60 to open and close, to regulate air flow to the chambers 58. Aromatic supply tubes or conduits 62 are mounted to communicate with the chambers 58 within the housing at their lower ends. The conduits extend upwardly through the boom 35 and intermediate the arms 31 and 32 of the bracket 30 to an injector header 64 mounted along the venturi nozzle 22. As air is introduced into the chambers 58, the aromatics in the containers are entrained in the air flow and are conveyed through the deliver or supply conduits to the injection header. The injection header includes a plurality of pressure operated valves 65 which open in response to the pressure in the conduits 62. When the valves 65 are opened, the aromatic air from the conduits is injected through nozzles 66 into the venturi passageway where the aromatics are mixed with the air from the plenum and discharged to the discharge mask 21 to an individual or patient. Again, the orientation of the valves 65 is restrained by the bracket 30 which limits pivoting of the delivery head 20 to an angle which ensures that the valves are maintained at least 100 above the horizontal plane to thereby facilitate drainage of condensed aromatics, when the valves 65 close to the venturi.

In the invention, the pressure actuated check valves are located as near to the injection point as possible. The injector nozzles extend into the venturi air stream in order to minimize residue. They rely on the assistance of the fast moving low pressure air to draw the aromatic pre-mix into the air stream for final mixing. The venturi creates a low pressure zone adjacent to the injector nozzles, helping to quickly diffuse the essence particles. This is necessary to prevent the residue from the many different scents from coating any shared surfaces they might contact. In this respect, the injectors are removable for cleaning or replacement, and are secure by slip fit or retaining ring in the injector headers.

As opposed to communicating the tubes 56 and the aromatic supply conduits 62 with the chambers 58, such tubes and conduits may communicate directly with each of the aromatic containers 50, such as through a removable cap on each container. Also the conduits 62 may be removable for cleaning or replacement, and may be part of a closed system with the containers and pneumatic valves and injectors, designed to prevent residue from polluting the system. Each conduit and container and pneumatic valve and injector may be handled as a single component, to be changed or replaced as a unit.

With specific reference to FIG. 1, it should be noted that the base 28 of the deliver apparatus may also include a shelf 70 which may be utilized to support containers as they are filled for placement into the pockets of the housing 42. This shelf is also used for general maintenance and cleaning of device components, etc. It supports small tools, brushed, solvents, etc. as required for cleaning and servicing the device.

With specific reference to FIG. 5, the internal control circuit for operating the blower 25, air pump 54 and the electro-mechanical valves 59 of the header assembly within the housing 42 is shown. A controller 60 is electrically connected to vary the blower speed rate in order to increase the pressure and/or velocity of air flowing from the discharge mask outlet. Further, the controller controls the air pump pressure and also controls the electro-mechanical valves associated with the header 55 to open and close the air supply valves in accordance with either manual or programmed input to supply air to the air supply lines 56 to the containers 50 within the chambers 58. The pressurized air entrains the aromatic substances and transports the aromatic substances through the supply conduits 62 to the pneumatic valves and injectors associated with the venturi. Again, the conduits extend at least partially vertically from the chambers 58 to the valves 65 and injector nozzles 66 to facilitate return of any condensed aromatics back to the chambers 58.

Figure 6:
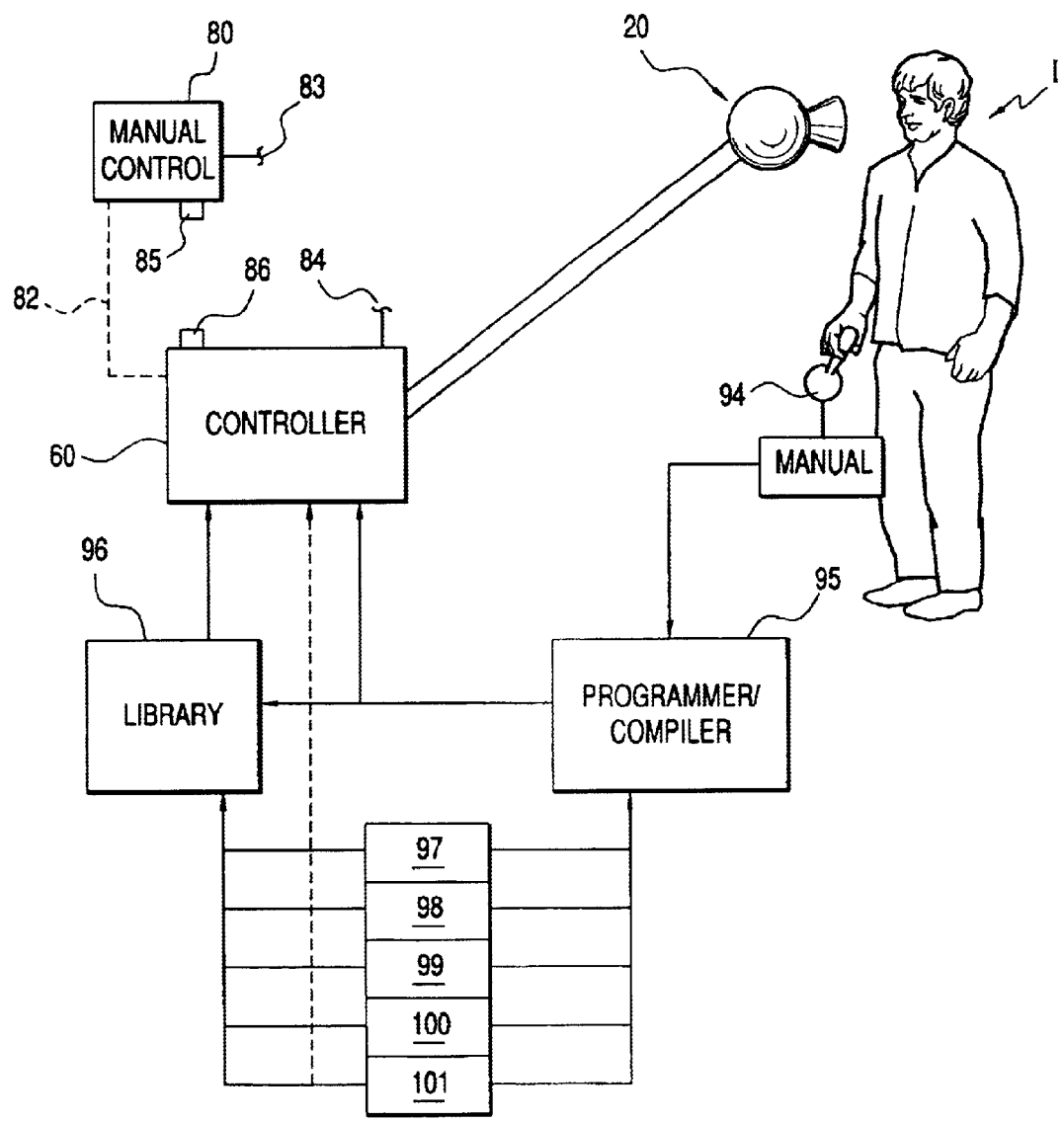
FIG. 6 is a program flow chart for use with the controller of the present invention.

The controller 60 mounted within the apparatus is operatively linked to one or more receivers which receive input from any one of a number of input devices. As shown in the schematic of FIG. 6, the controller may receiver manual input 82 by way of conventional electrical circuits 80 which may be hardwired to the controller and which my include various switches, dials and the like which are manually manipulated to effect the output of the controller 60 in order to control the discharge of one or more of the aromatics. As opposed to direct connections, various input devices including remote control devices can be used to transmit either RF (Radio Frequency) signals from a remote transmitter 83 to a receiver 84 mounted on the apparatus housing. As opposed to a radio transmitter, optical signals may be transmitted from an optical transmitter 85 to a sensor 86 also mounted to the apparatus housing.

The delivery apparatus of the present invention can be controlled by a number of source methods which are operable in various modes. The controller may be operatively connected to conventional circuits including switches, computer touch screens or similar inputs 94 operable by the individual receiving olfactory stimulation treatment of therapy. The input 94 may be connected to a programmer 95 which may interface directly with the controller 60 or indirectly through a library 96 which retains information specific to the individual.

As opposed to patient or user control, the controller and related systems of the invention may be operated by a technician input 97. The technician may vary the aromatic treatment based upon patient response or other criteria.

In addition to the foregoing, computer assisted programs 98 can be made to be interactive with the controller 60 of the invention and user biofeedback can be combined with system control. Further, the programs can provide event queues or blends of various aromatic substances. In some instances, remote control of the delivery apparatus may be provided by intranet or internet connections 100 allowing remote providers to control the delivery of aromatic substances to an individual. Such remote inner activity can allow individuals to download scent compositions received from others or which may be combined with other types of media such that an individual may receive a media over the internet which is preprogrammed to control the delivery of aromatic substances in a coordinated manner.

In addition to the foregoing, recorded media queues including music CDs, DVDs, video, TV, game and game machines 101 may be made to be interactive so as to trigger distribution of various blends of aromatic substances by direct link to the controller 60 of the present invention or through the library 96 to the controller.

Figure 7:
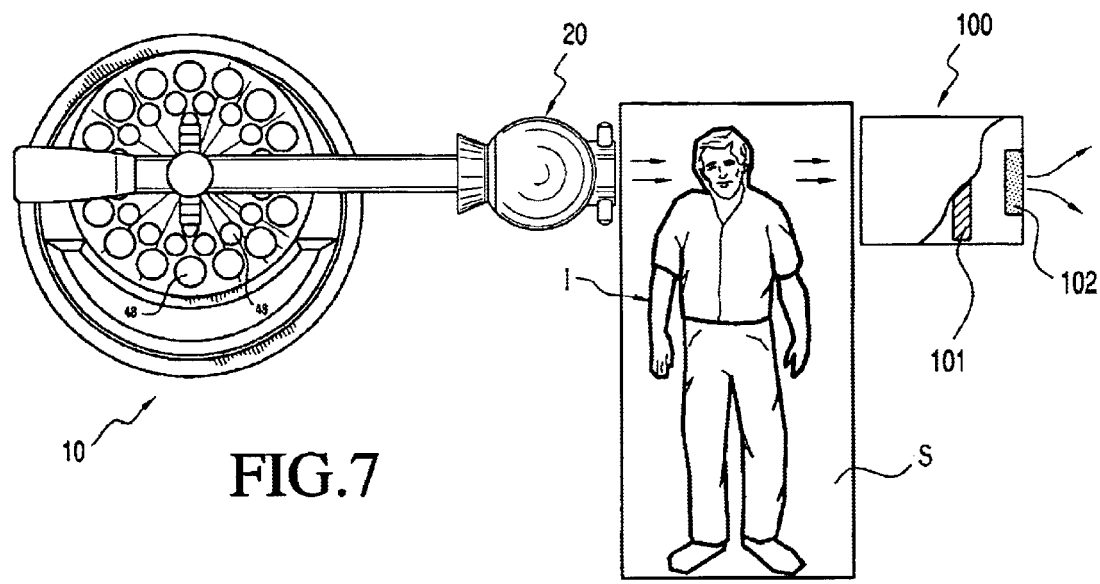
FIG. 7 is a top plan illustrational view of one embodiment of the invention in use.

With particular reference to FIG. 7, the delivery apparatus 10 of the present invention is further shown in use in delivering aromatic substances to an individual "I" supported on a support "S" such as a couch, table, massage platform or the like. In order to limit the amount of distribution of the aromatic substances from the delivery apparatus to the surrounding atmosphere, the invention also contemplates a system wherein a delivery apparatus is used in conjunction with a filter device 100. The filter device may be a separately controlled unit which may be placed downstream of the individual or patient receiving the aromatic substances delivered from the apparatus of the invention. The downstream filter unit includes a filter element 101 and a blower or fan assembly 102 for urging the air entrained with the various aromatics through the unit to remove the aromatic substances such that they do not enter the surrounding atmosphere after passing downstream of the individual or patient receiving treatment or therapy. In this manner, the surrounding atmosphere in the area in which the delivery apparatus is operated is not adversely contaminated by the aromatic substances being delivered to a patient.

Figure 8:
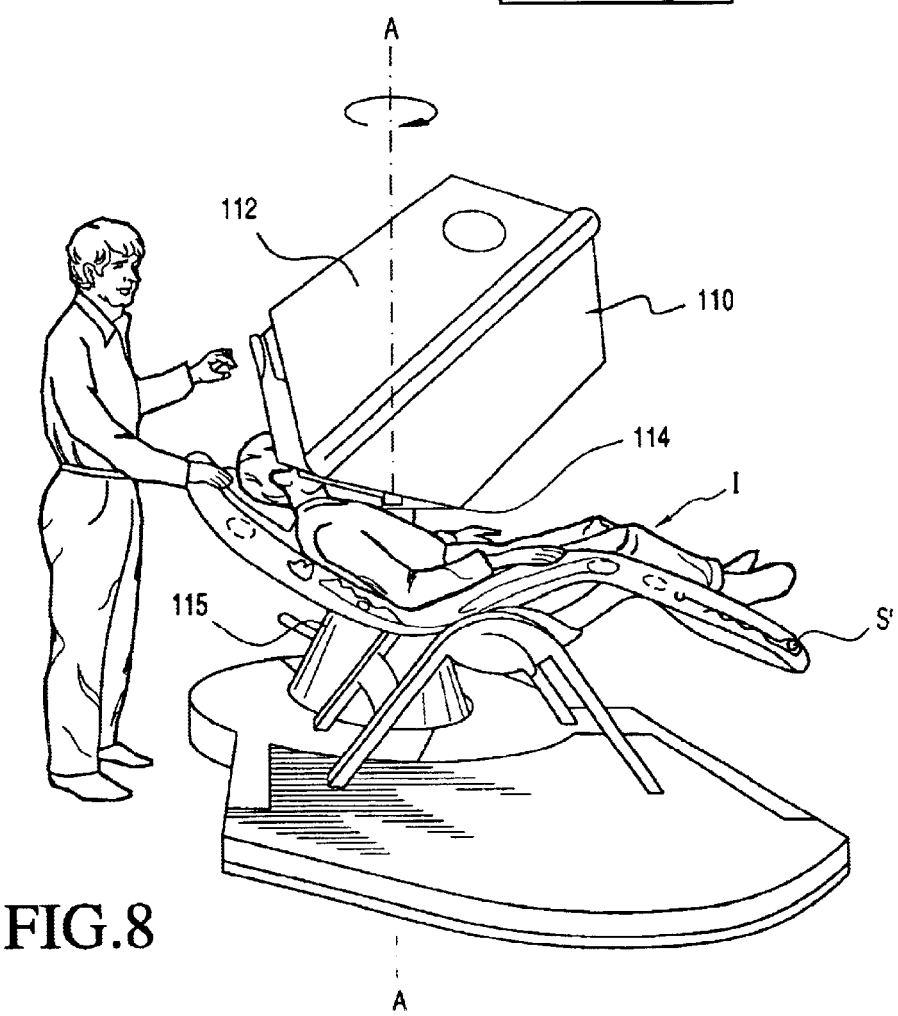
FIG. 8 is a perspective illustrational view of a second embodiment of the invention.
Figure 9:
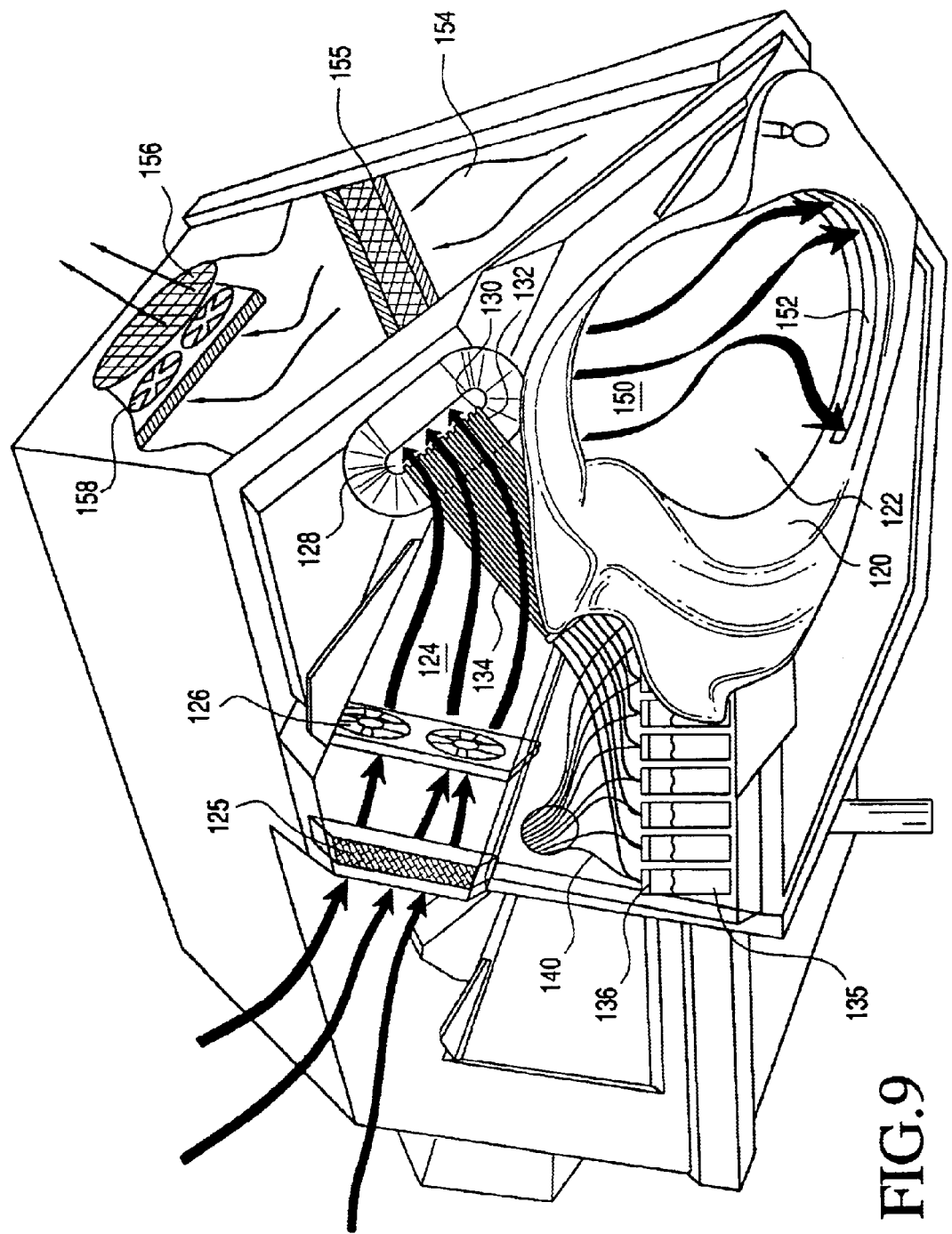
FIG. 9 is a perspective partial cross sectional view of the embodiment of FIG. 8.

With specific reference to FIGS. 8 and 9, another embodiment of delivery apparatus 110 in accordance with the teachings of the present invention is shown. In this embodiment, the individual "I" receiving olfactory treatment or therapy is supported by a support "S'", such as the chair shown in drawing FIG. 8, so as to be supported relative to an enlarged housing 112 which is pivotally mounted about a vertical axis "A—A" as shown by the arrow in the figure to a support post 114 carried by a stand 115.

As shown on FIG. 9, the housing 112 includes a mask 120 which surrounds a discharge opening 122. The mask is designed to allow an individual to place their face centrally of the opening 122 with the mask 120 surrounding the individual's face, as is generally shown in FIG. 8, when the individual is in the seat or support "S'" and the housing 112 rotated to the position shown.

As with the previous embodiment, the present embodiment provides a venturi mixing of aromatic substances with air flow through the housing 112. In this respect, the housing includes an inner plenum chamber 124 into which air enters through a prefilter 125 mounted at an air intake opening into the housing after which the air flow passes through blowers or fans 126 so that the air enters the plenum chamber. At the exit end of the plenum chamber is a venturi nozzle 128 which is similar to that as described at 22 with respect to the embodiments of FIGS. 1–7. In the venturi nozzle 128, aromatic essences or substances are injected by nozzles 130 connected to pressure activated injector valves 132, both of which are similar to those described with respect to the previous embodiment. The aromatic substances are provided to the valves 132 by way of conduits 134 which extend to aromatic containers 135 mounted within the housing. Each of the containers 135 includes a cap or top 136 through which the conduits 134 enter into an air space above the aromatic substance contained within the containers.

As with the previous embodiment, it should be noted that the conduits 134 extend so as to include a vertical component along their full length into the containers 135 so as to provide a gravity drain along the conduits from the nozzles 130 to the containers 135.

Pressurized air is provided to the containers 135 through a plurality of conduits 140 which extend to a distribution header mounted within the housing but not being shown. The distribution header is similar to that as shown at 55 in FIG. 5 concerning the embodiments of FIGS. 1–7. Also mounted within the housing is a controller (not shown) similar to controller 60 of FIG. 5 which controls the operation of an air pump (not shown) which is also similar to that shown at 54 in FIG. 5. The controller in the present embodiment may be operated in the same manner as disclosed with respect to the previous embodiment in order to regulate the flow of air and the air pressure within the air supply tubes 140 to the aromatics substance containers 135 to thereby entrain the aromatic substances in the conduits 134 20 supplying the venturi 128.

After the aromatic substances are injected into the air flow in the venturi 128, the air flow is directed into a down stream chamber 150 which communicates with the opening 122 into the mask 120. The arrows show the general flow of the air which has the aromatic substances entrained therein. The air flow is across the mask and into a downstream inlet 152 which communicates through a separate portion of the housing, as shown at 154, through a filter 155 to an air discharge outlet 156. The air flows by one or more fans or blowers as shown at 158. In this manner, once the air having the aromatic substances entrained passes through the chamber 150 communicating with the opening 122, the air and substances are conveyed and filtered so as to remove any aromatic substances before the air is discharged through the outlet opening 156.

In the present embodiment, the use of the venturi 128 ensures a thorough mixing of the aromatic substances with the air flow from the plenum chamber. Further, as with the previous embodiment, the nozzles 130, valves 132, fluid conduits 134 and/or the aromatic substance container 135 may be provided as a replaceable unit or with each one of the conduits nozzles and valves being replaceable as a unit extending between the containers and the venturi.

In FIG. 9, the side and a portion of the front panel of the housing has been removed to show the movement of the air flow through the filters, blowers, and venturi and as well as to show the conduit location between the venturi and the aromatic substance containers of the present invention. The housing may take other configurations and yet be within the teachings of the present invention.

As with the previous embodiment and as shown in FIG. 7, the present embodiment provides not only a means for supplying aromatic substances to an individual or patient after being entrained within air flow passing through a venturi, but the present invention further provides for the filtration of the air after passing the individual or patient, such that the aromatic substances are completely removed before air flow from the apparatus exits into the environment surrounding the housing 112.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents.

I claim:

1. An apparatus for delivering air flow for olfactory stimulation or therapy to an individual having at least one selected aromatic substance entrained therein including a plenum housing, a plurality of aromatic substance containers mounted relative to said plenum housing, means for selectively supplying a first air flow relative to at least one predetermined one of said containers in a manner to entrain at least one aromatic substance therein, conduit means extending from said containers to a venturi nozzle associated with said plenum housing disposed upstream thereof, means for introducing secondary air flow into said plenum housing and toward said venturi nozzle, injector means for injecting air entrained with at least one aromatic substance from said conduits into said venturi nozzle to thereby mix said at least one substance within said secondary air flow and a discharge outlet downstream of said nozzle for discharging air having at least one aromatic substance entrained therein to an individual.

2. The apparatus of claim 1 including means spaced from said discharge outlet for receiving the mixed air having at least one aromatic substance entrained therein after passing in proximity to the individual, said means for receiving including filtration means for removing aromatic substances.

3. The apparatus of claim 1 in which said conduit means have a substantially continuous vertical component of orientation between said plurality of containers and said venturi nozzle such that said plurality of conduit means drain liquids therein toward said plurality of containers.

4. The apparatus of claim 3 including means for selectively controlling the supply of the first air flow to said containers.

5. The apparatus of claim 1 including means for controlling said means for selectively supplying the first air flow such that aromatic substance from said plurality of containers are selectively entrained dependent upon programmed input relating to a particular individual.

6. A method for individual olfactory stimulation or therapy using an airflow having at least one selected aromatic substance entrained therein comprising the steps of:
   a. providing a plurality of containers having aromatic substances therein;
   b. providing a first air flow and selectively entraining at least one of the substances from a predetermined one said plurality of containers into the first air flow and conveying the at least one substance entrained with the first air flow to a venturi upstream of a discharge outlet of a plenum chamber, passing a second air flow through the plenum chamber and into said venturi so as to mix with said first air flow having said at least one substance entrained therein; and
   c. discharging the mixed first and second air flows from the discharge outlet of the plenum chamber relative to an individual to receive olfactory stimulation or therapy.

7. The method of claim 6 including the additional step of conveying said mixed first and second air flows into a filtration apparatus after the first and second air flows have passed the individual receiving olfactory stimulation or therapy.

8. The method of claim 6 including adjustably supporting the plenum chamber such that the discharge outlet may be selectively oriented with respect to an individual.

9. The method of claim 6 including selectively controlling the first air flow relative to the plurality of containers such that the first air flow communicates with an aromatic substance in at least one predetermined of the plurality of containers to entrain the aromatic substance therein.

10. The method of claim 9 including using a controller to selectively control the first air flow, wherein the controller is responsive to biofeedback received by an individual undergoing olfactory stimulation or therapy.

11. The method of claim 9 including using a controller to selectively control the first air flow and wherein the controller is responsive to input from a library source which supplies information specific to a individual undergoing olfactory stimulation or therapy.

12. The method of claim 9 including using a controller to selectively control the first air flow and wherein the controller is responsive to input from media queues to provide different aromatic substances to an individual.

13. An apparatus for delivering air flow for olfactory stimulation or therapy to an individual having at least one selected aromatic substance entrained therein including a base, a plenum housing, means for adjustably mounting said plenum housing to said base, a plurality of aromatic substance containers, means for supplying a first air flow to said containers in a manner to entrain aromatic substances therein, a plurality of conduit means extending from said containers to a plurality of injector means mounted to a venturi nozzle extending from said plenum housing, means for introducing a secondary air flow into said plenum housing and toward said venturi nozzle, said injector means injecting the first air flow entrained with at least one aromatic substance from said plurality of conduit means into said venturi nozzle to thereby mix said at least one substance within said secondary air flow and a discharge outlet downstream of said venturi nozzle for discharging mixed air having at least one aromatic substance entrained therein to an individual.

14. The apparatus of claim 13 including means spaced from said discharge outlet for receiving the mixed air having at least one aromatic substance entrained therein after passing in proximity to the individual, said means for receiving including filtration means for removing aromatic substances.

15. The apparatus of claim 13 wherein said means for supplying a first air flow includes an air supply source mounted on said base, said air supply source being selectively connected by way of a plurality of first valve means to said plurality of containers, and means for selectively controlling said first valve means to entrain aromatic substances within said plurality of containers in said first air flow.

16. The apparatus of claim 15 including a boom adjustably mounted to said base, means for adjustably mounting said plenum housing to an upper portion of said boom, and said plurality of conduit means being mounted within said boom.

17. The apparatus of claim 16 including means for limiting a vertical adjustment of said boom relative to said base such that said boom is maintained at an angle above a horizontal plane to thereby assist drainage of liquids within said plurality of conduit means toward said plurality of containers.

18. The apparatus of claim 13 wherein each of said injector means includes a pressure operated normally closed valve for normally closing an upper end of said plurality of conduit means.

19. The apparatus of claim 18 wherein said plurality of injector means are removably mounted to said venturi nozzle.

20. The apparatus of claim 13 in which said means for introducing a secondary air flow includes a fan means for drawing ambient air into said plenum chamber through a filter element.

* * * * *